United States Patent [19]

Miller et al.

[11] Patent Number: 5,443,473
[45] Date of Patent: Aug. 22, 1995

[54] METHOD FOR TREATING MYOPIA

[75] Inventors: David Miller, Brookline; Edward Perez, Cambridge, both of Mass.

[73] Assignee: Anika Research, Inc., Woburn, Mass.

[21] Appl. No.: 117,153

[22] PCT Filed: Mar. 15, 1992

[86] PCT No.: PCT/US92/02100

§ 371 Date: Feb. 16, 1994

§ 102(e) Date: Feb. 16, 1994

[87] PCT Pub. No.: WO92/16172

PCT Pub. Date: Oct. 1, 1992

Related U.S. Application Data

[63] Continuation-in-part of Ser. No. 670,340, Mar. 15, 1991, abandoned.

[51] Int. Cl.⁶ .................................................. A61B 17/32
[52] U.S. Cl. .................................. 606/166; 606/107; 623/5
[58] Field of Search .................... 606/166, 161, 107; 128/898; 623/5

[56] References Cited

U.S. PATENT DOCUMENTS

| | | | |
|---|---|---|---|
| 4,607,617 | 8/1986 | Choyce | 128/1 R |
| 4,959,070 | 9/1990 | McDonald | 623/6 |
| 4,994,081 | 2/1991 | Civerchia et al. | 623/5 |

FOREIGN PATENT DOCUMENTS 2631545  5/1988  France .

OTHER PUBLICATIONS

Biodomi, "Fexible lens epi-corneal implantation instrument—has spatula rotating about application pad inserting lens periphery in excision," (From *Derwent Publications, Ltd.*, London, GB, 24 Nov. 1989) (Abstract No. from FR2631-545-A (Ref. AL, above)).

Werblin, T. P. et al., "Eight Years Experience with Permalens Intracorneal Lenses in Nonhuman Primates," *Refractive & Corneal Surgery*, 8:12–22 Jan./Feb. 1992.

Beekhuis, W. H. and McCarey, B. E., "Hydration Stability of Intracorneal Hydrogel Implants," *Investigative Opthalmology & Visual Science*, 26:1634–1636 Nov., 1985.

Choyce, P. D., "Update on Polysulfone Corneal Inlays," *Cataract and Refractive Microsurgery*, pp. 285–290. (1989).

*Primary Examiner*—Michael H. Thaler
*Attorney, Agent, or Firm*—Hamilton, Brook, Smith & Reynolds

[57] ABSTRACT

A method for treating a myopic eye or eye with other refractive errors is provided. The method includes forming a circular cut in the anterial lamina of the cornea, forming a pocket in the lamella beneath the weakened anterial lamina, and inserting an intrastromal lens within the pocket to alter the radius of curvature of the anterial lamina. Devices for weakening the anterial lamina and for forming the pocket within the lamella are also disclosed.

4 Claims, 1 Drawing Sheet

METHOD FOR TREATING MYOPIA

This application is a continuation-in-part of U.S. Ser. No. 670,340, filed Mar. 15, 1991 now abandoned.

BACKGROUND OF THE INVENTION

Myopia or "nearsightedness" is most commonly treated by the use of eye glasses or contact lenses. Occasionally, however, a myopic person cannot or does not wish to rely on glasses or contact lenses. In recent years, in limited cases, myopia has been surgically treated by a procedure called a "radial keratomy." In this procedure a series of cuts arranged like the spokes of a wheel are made in the cornea. The cuts produce a flattening of the corneal curvature and, if successful, thereby correct the myopia. The procedure, which was developed in Russia, has met with only limited acceptance by surgeons in the United States.

The radial keratomy method has two drawbacks: (1) it can never have a fully predictable outcome and (2) any non-spherical flattening of the cornea during healing will result in an eyesight defect which cannot be corrected by the use of eye glasses or contact lenses.

A modification of the radial keratomy procedure, called keratoprosthesis, was recently developed in the United States. In this procedure a lamellar keratoplasty is performed in which only the superficial layer of the cornea is removed and replaced with a corneal implant. These implants are a replacement for the natural cornea where the cornea has become opaque-or fogged as may occur as the result of burns. This procedure, if successful, also tends to flatten the cornea and hence remove the cause of the myopia. Like the radial keratomy procedure the lamellar keratoplasty is traumatic to the patient and the patient may experience difficulty during the healing process such as infection, epithelial cell granulations, scar tissue foundation and the like.

After a keratoprosthesis is inserted between the layers of the natural cornea a window is cut out of at least the damaged outer layer to permit the eye to see through the prosthesis. If the inner layer of the cornea is undamaged then it is only necessary to trephine the outer layer of the cornea leaving the aqueous humour separated from the surrounding air by the inner layer of the cornea backed by the keratoprosthesis. Should the inner layer of the cornea also be damaged then it too must be removed leaving the prosthesis as the only layer between the aqueous humour and the ambient air. Thus, the keratoprosthesis is always in contact with the air and is held in place by the portions of the natural cornea which remain only around its periphery.

Choyce, U.S. Pat. No. 4,607,617, describes a method for correcting an eyesight defect in which an implant made from polysulfone plastics material is inserted into a pocket formed in the cornea. This polysulfone lens has a refractive index which is greater than the refractive index of the cornea itself. Thus, Choyce alters the optical power of the cornea by inserting a plastic lens which has a high refractive index. However, the use of a plastic lens does not allow a sufficient amount of the fluid circulating in the cornea to reach the cornea tissue in front of the lens; as a result, this tissue may suffer tissue rot from a lack of nutrition.

It is thus an object of this invention to provide a method for correcting a refractive error in an eye where the method is not characterized by the foregoing problems. It is another object of the invention to provide an improved surgical procedure for the treatment of myopia, hyperopia, astigmatism or aphakia. It is yet another object of the invention is to provide such a treatment for myopia which is less invasive than surgical procedures heretofore practiced. It is still another object of the invention to provide the implements with which the procedure may be practiced.

SUMMARY OF THE INVENTION

In accordance with the present invention a shallow circular cut is made in the surface of the cornea of a myopic eye or those of the other refractive errors. The depth of the cut is limited so as to extend to just below the anterial lamina (Bowman's membrane) which maintains the curvature of the cornea. A small incision is then made in the cornea adjacent to the circular cut to a depth beneath the Bowman's membrane to gain entrance to the layer of cells and fibers positioned there. This layer, which is approximately 200 fiber layers thick, has its fibers laid out in layers which can be separated from one another. A keratome or other surgical knife is inserted through the incision and used to separate the layers to form a pocket. An intrastromal implant in the form of a lens of a hydrogel is then introduced into the pocket. The incision is sealed by applying a biological glue or plaster to the site.

The lens within the corneal stroma in conjunction with the severed Bowman's membrane serve to flatten and hold the cornea in a flattened state to correct the myopic condition or to modify the curvature for the other refractive errors.

The trephine used to cut the Bowman's membrane and the keratome used to separate the lamella beneath the Bowman's membrane are provided with governors to limit their respective penetrations.

Other objects, features and advantages of this invention will be apparent to those skilled in the art from the following detailed description of preferred embodiments taken together with the accompanying drawings.

DETAILED DESCRIPTION OF THE PREFERRED EMBODIMENT OF THE INVENTION

In general, the invention relates to a method for improving eyesight. In particular, the invention is directed to a method for treating myopia by altering the radius of curvature of the cornea.

The accompanying drawings illustrate an eye operation for modifying the refractive index of the cornea. The method involves weakening the anterial laminar of the cornea and then inserting a intrastromal lens into a pocket in the cornea to modify the radius of curvature of the cornea.

The intrastromal lens is preferably a hydrogel lens. A hydrogel is a dimensionally stable polymer which has open spaces that are occupied by water molecules. The hydrogel of this invention has a water content of greater than 50%, and preferably about 80%. Thus, the hydrogel lens allows nutrients to pass through it to reach the front of the cornea. The hydrogel lens has a refractive index substantially equal to the refractive index of the cornea. Suitable hydrogel lenses may be obtained from Permalens, Vistamarc ®, Ethafilcon and Lidofalcon. See, for example, Beekhuis W. and McCarey B., Investigative Ophthalmology & Visual Science, 26:1634–1636.

Figure 1:
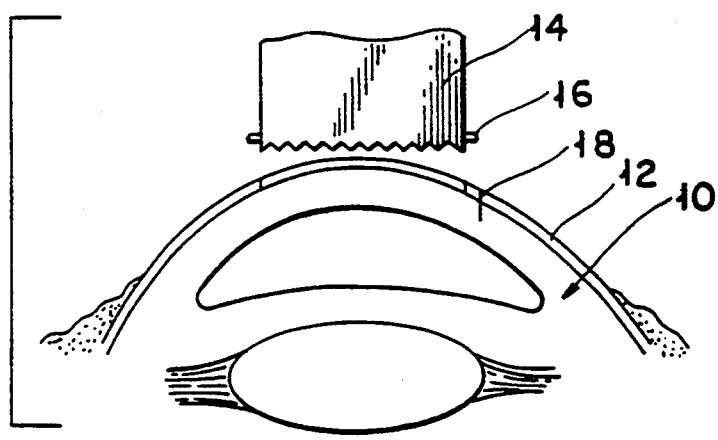
FIG. 1 shows a cross-section of a cornea and trephine used to form a circular cut therein.

Reference is now made to the drawings and to FIG. 1 in particular wherein a simplified view of a cornea 10 of a myopic eye is depicted. As will be appreciated the myopia is caused by the eye becoming too long so as to prevent rays of light from distant objects from properly focusing on the retina. The curvature of the cornea is maintained by the very inflexible and strong anterial laminar (Bowman's membrane) 12. In accordance with the present method the Bowman's membrane is first weakened by forming a cut with a trephine 14 containing a governor 16 or having teeth of a height to limit the cut to only penetrate the Bowman's membrane. The cut formed with the trephine is circular.

Figure 2:
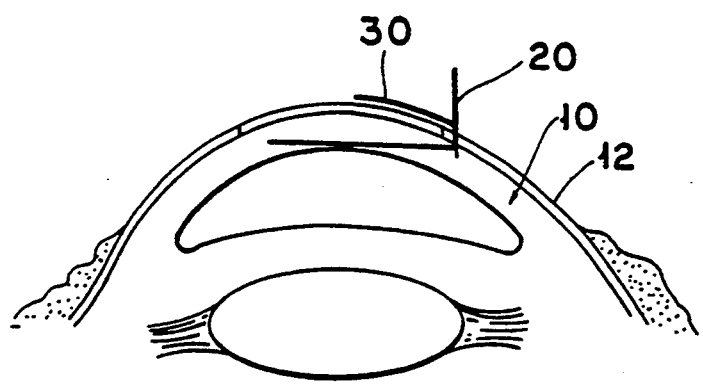
FIG. 2 shows a cross-section of the cornea of FIG. 1 with a keratone inserted in an incision in the cornea.
Figure 3:
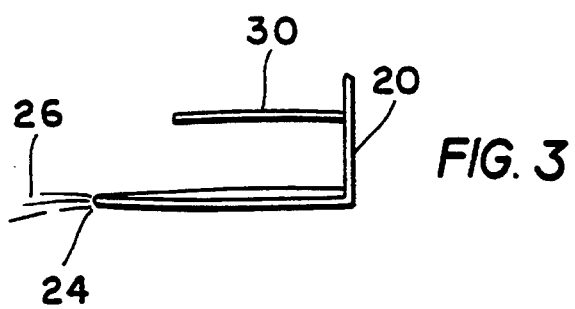
FIG. 3 shows a cross-section of a keratone which can be used to form a pocket in the cornea.

An incision 18 is then formed adjacent the circular cut formed with the trephine. Incision 18 extends to the lamella beneath the Bowman's membrane which is approximately 200 microns in thickness. The fibers of the lamella are laid out in layers which may be separated from each other. As shown in FIG. 2, a surgical knife or keratome 20 is inserted into the incision 18 to the layer below the Bowman's membrane and oscillated so as to form a pocket 22 in the lamella. The keratome 20 has a blunt tip and is generally designed similar to a spatula. Keratome 20 preferably has an irrigation tip through which a water jet 26 may flow to aid in separating the cell layers and open the tissue plane as shown in FIG. 3. The keratome 20 is further provided with a governor 30 which controls the depth of penetration and separation.

Figure 4:
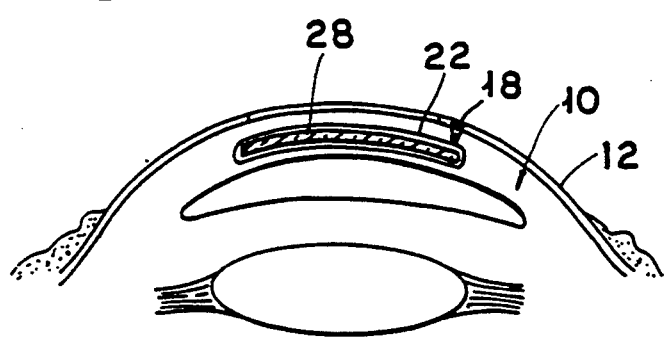
FIG. 4 shows a cross-section of the cornea shown in FIG. 1 after insertion of an intrastromal implant in the pocket formed below the Bowman's membrane.

After the pocket 22 is formed below the Bowman's membrane, an intrastromal lens 28 is inserted into the pocket through incision 18. Preferably, the intrastromal lens 28 is a hydrogel lens which is folded to facilitate its insertion in the pocket 22, and then it is permitted to unfold once within the pocket. Alternatively, the hydrogel lens can be introduced into the pocket using a forked instrument. A fine rod formed with a notch in its end is then used to prod the lens into its desired position. Finally, to prevent entrance of surface epithelial cells, the incision should be packed with a biological glue or surgical plaster (i.e., fibrin and collagen or fibrin alone) as shown in FIG. 4. Alternatively, the incision 18 can be sutured. However, the biological glue or surgical plaster is preferably used because sutures have a tendency to distort the optics.

The combination of the hydrogel lens 28 and the weakened Bowman's membrane 12 cooperate to flatten the cornea and thereby alter its radius of curvature. The change in the radius of curvature will correct the myopic condition.

Since there is no removal of corneal tissue the trauma to the eye is greatly reduced as compared with other surgical procedures for correcting myopia. Further, healing is much more rapid.

The foregoing description should be taken as illustrative and not limiting in any sense. Other embodiments of the invention will occur to those skilled in the ant and are within the scope of the following claims.

I claim:

1. A method for changing the radius of curvative of the cornea of an eye to correct a refractive error, comprising the steps of:
    a) forming a first circular incision partially into the anterial lamina of the cornea of the eye to weaken said anterial lamina;
    b) forming a second incision which is separate from and adjacent to said first incision, said second incision extending into the lamella of the cornea to form a pocket within the lamella beneath the weakened anterial lamina;
    c) enclosing a hydrogel lens within said pocket, said hydrogel lens having a refractive index substantially equal to the refractive index of the cornea and said hydrogel lens cooperating with said weakened anterial lamina to change said radius of curvature of said cornea and thereby correct said refractive error; and
    d) closing said second incision, thereby sealing said hydrogel lens within the alamella.

2. The method of claim 1, wherein said pocket is formed by a keratome inserted through said second incision.

3. The method of claim 2 further comprising the step of directing a water spray through said keratome to form said pocket.

4. The method of claim 1 wherein said sealing step comprises applying a surgical plaster to said second incision.

* * * * *

UNITED STATES PATENT AND TRADEMARK OFFICE
CERTIFICATE OF CORRECTION

PATENT NO. : 5,443,473

DATED : August 22, 1995

INVENTOR(S) : David Miller and Edward Perez

It is certified that error appears in the above-identified patent and that said Letters Patent is hereby corrected as shown below:

Column 4, line 39:  Delete "alamella" and insert therefor --lamella--.

Signed and Sealed this

Twenty-first Day of November, 1995

Attest:

BRUCE LEHMAN

*Attesting Officer*  *Commissioner of Patents and Trademarks*